(12) United States Patent
Chehab et al.

(10) Patent No.: US 9,402,672 B2
(45) Date of Patent: Aug. 2, 2016

(54) JOINT DISTRACTION DEVICE FOR ARTHROSCOPIC SURGERY

(71) Applicant: The Board of Trustees of the Leland Stanford Junior University, Palo Alto, CA (US)

(72) Inventors: Eric Fayez Chehab, San Francisco, CA (US); Archana Appukuttan Nair, Eden Prairie, MN (US); Chad Alexander Sitgraves, Englewood, NJ (US); Marc Raymond Safran, Stanford, CA (US)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 0 days.

(21) Appl. No.: 14/530,500

(22) Filed: Oct. 31, 2014

(65) Prior Publication Data

US 2015/0057668 A1 Feb. 26, 2015

Related U.S. Application Data

(63) Continuation of application No. PCT/US2013/039117, filed on May 1, 2013.

(60) Provisional application No. 61/641,302, filed on May 2, 2012, provisional application No. 61/718,011, filed on Oct. 24, 2012.

(51) Int. Cl.
*A61B 17/88* (2006.01)
*A61B 17/02* (2006.01)

(52) U.S. Cl.
CPC ............. *A61B 17/885* (2013.01); *A61B 17/025* (2013.01); *A61B 2017/0268* (2013.01); *A61B 2017/0275* (2013.01)

(58) Field of Classification Search
CPC .................... A61B 17/885; A61B 2017/0268; A61B 17/025
USPC ........................................ 606/90, 105, 86 R
See application file for complete search history.

(56) References Cited

U.S. PATENT DOCUMENTS

| | | | |
|---|---|---|---|
| 2009/0281545 A1* | 11/2009 | Stubbs | A61B 17/1666 606/87 |
| 2010/0179655 A1* | 7/2010 | Hansell | A61F 2/44 623/17.11 |
| 2011/0166579 A1* | 7/2011 | Deem | A61B 17/025 606/90 |

* cited by examiner

*Primary Examiner* — Christopher Beccia
(74) *Attorney, Agent, or Firm* — William A. English; Vista IP Law Group LLP

(57) ABSTRACT

A joint distraction device for use in an arthroscopic surgery is provided. The device has a joint distraction mechanism, situated in between two bone fixation surfaces, and is capable of changing the relative distance between these two surfaces. The force generated by the mechanism should be sufficient to insert bone spikes affixed to the surfaces into bone, as well as distract the joint to create a sufficient enough gap to allow the intended procedure. With the surfaces and spikes engaged to bone at opposite sites of a joint, an increase in distraction force results in an increase in the relative distance results, hence increasing the space within the joint. Embodiments of this invention, compared to fracture table approaches, effectively eliminate the risk of pudendal nerve injury, allow for longer surgical times, and allow for much more controllable joint distraction.

15 Claims, 3 Drawing Sheets

JOINT DISTRACTION DEVICE FOR ARTHROSCOPIC SURGERY

RELATED APPLICATION DATA

This application is a continuation of co-pending International Application No. PCT/US2013/039117, filed May 1, 2013, which claims priority to provisional application Ser. No. 61/641,302, filed May 2, 2012, and Ser. No. 61/718,011, filed Oct. 24, 2012, the entire disclosures of which are expressly incorporated by reference herein.

FIELD OF THE INVENTION

The invention relates to joint distraction devices and surgical procedures.

BACKGROUND OF THE INVENTION

Hip arthroscopy is becoming an increasingly common and effective surgery as it allows for the repair and resurfacing of various parts of the hip with minimal surgical trauma to the patient. However, such a procedure requires distraction of the femoral head from the acetabulum of the pelvis to allow for arthroscopic access to the tissues within the joint.

The hip is a constrained joint, and has an anatomical structure similar to a 'tight' ball and socket joint. Therefore, distraction requires, relatively speaking to other joints, a fairly large amount of traction force to create a space in the joint that is adequate for the surgical procedure.

The current distraction device standard for hip arthroscopy is the fracture table where the femoral head is distracted from the acetabulum by pulling the leg away from the pelvis to create sufficient joint space. Counter-traction is achieved by placing a fixed post placed at the patient's groin. The fracture table procedure is a crude and imprecise mechanism that may give risk to postoperative complications such as pudendal nerve injury and other joint (e.g., ankle or knee) damage. Accordingly, there is a need in the art to develop a technology with the goal to reduce such postoperative complications for the patients while maintaining adequate joint space in the hip for arthroscopic surgery.

SUMMARY

The present invention provides a joint distraction device for use in an arthroscopic surgery. The device can be arthroscopically inserted within a body or inserted via an open incision. A joint distraction mechanism is situated in between a proximal and distal bone fixation surface. The proximal end and the distal end of the joint distraction mechanism are affixed respectively to a proximal fixation surface and a distal fixation surface.

The proximal fixation surface has an outer facing surface facing away from the joint distraction device. This outer facing surface has two or more bone spikes for engagement with a proximal bone segment proximally located to a joint. The distal fixation surface has an outer facing surface facing away from the joint distraction device. In one embodiment, this distal fixation surface has one bone spike for engagement with a distal bone segment distally located from the joint. In another embodiment, this distal fixation surface could have two or more bone spikes. The bone spikes, screws or other projections to allow fixation (temporary or permanent) are typically connected substantially perpendicular to the respective outer surfaces of the fixation surfaces.

The joint distraction mechanism has a force driving mechanism for changing the relative distance between the proximal fixation surface and the distal fixation surface. Examples are provided of a worm gear force driving mechanism or a pneumatic force driving mechanism. This joint distraction mechanism is useful to change the relative distance between the proximal bone segment and the distal bone segment. The force generated should be sufficient to insert the bone spikes (in case they are not screws and do not have to be screwed into the bone), as well as sufficient to distract the joint (i.e., create a sufficient gap to allow the intended surgical procedure). With the surfaces and spikes engaged to bone at opposite sites of a joint, an increase in distraction force results in an increase in the relative distance results, hence increasing the space within the joint. The device is preferably in its shortened position during insertion into and removal from (e.g., arthroscopically) a patient's body.

The joint distraction device could further have: (i) an articulating joint or (ii) a fixed joint angle for aligning the relative position of the proximal fixation surface with the proximal bone segment. In other words, this is used for pointing two segments of the device in between the bone surfaces for better alignment. In one example, the articulating joint is a three-dimensional articulating joint. The articulating joint can be locked or fixed in a position useful when the distraction takes place.

Embodiments of the invention pertain to joint distraction devices and the use/application of such devices, which are described herein with potential advantages when compared to, for example, the use of the fracture table approach. One potential advantage pertains to the use of the device as it effectively eliminates the risk of pudendal nerve injury common with the fracture table approach. Currently, using the fracture table, surgical time is limited (usually to less than 2 hours) due to the risk of nerve injury from the pressure resulting from the traction-counter traction of the fracture table. With the device of this invention, it is conceivable that the duration of surgery would no longer be limited by fear of complications associated with the fracture table. This would allow for the development and practice of more advanced and complex surgical techniques and procedures. In addition, the device could be placed lateral to the joint and therefore does not obstruct the operating space of the surgeon. Furthermore, in contrast with the fracture table approach, the device allows for controllable distraction. Yet another advantage in the application to the hip joint is that by applying the distraction force along a line closer to parallel with the femoral neck, the overall force required to distract the hip is reduced.

DETAILED DESCRIPTION

Joint distraction devices according to the invention are intended to arthroscopically distract a joint by applying opposing forces to a proximal and distal bone segment crossing the joint. Specific examples herein relate to the hip joint, but the invention is not limited as such since these devices can be used for distraction of other joints as well, such the knee joint for meniscus or osteochondral grafting. It could also be used for the elbow joint for osteochondral grafting or soft tissue resurfacing. Further, the ankle joint is a candidate for the use of the device for open ankle surgery.

In the example of the hip joint, the device distracts the hip joint by applying opposing force to non-cartilagenous areas such as the anterior inferior iliac spine (AIIS) and the piriformis fossa. More generally speaking, the forces could be applied to areas on the pelvis and the proximal femur. For example, the device could be applied within the joint capsule or exterior to it. The device is inserted through a cannula under arthroscopic and fluoroscopic visualization starting in the peripheral compartment of the joint space. Fluoroscopic visualization is useful to ensure proper insertion and placement of the device. Fluoroscopy is especially useful for the placement to the piriformis fossa. Arthroscopy could be sufficient for the placement to the AIIS.

The device is inserted in a shortened position and expanded inside the patient. Removal of the device is the reverse order of the insertion procedure meaning that the expansion is reversed and the device is removed from the cannula in the shortened position. During the procedure, the cannula could be free for other instruments needed during surgery.

The expansion and shortening of the joint distraction device could either be done with a helical worm gear drive mechanism, a pneumatic cylindrical mechanism or a combination thereof. Once the device is inside the peripheral compartment (e.g., under muscle and can be in or outside the capsule), a proximal portion of the device goes on to the AIIS and a distal portion of the device goes into the piriformis fossa. Once this happens, distraction occurs as the device continues to be expanded and apply opposing forces to the AIIS and piriformis fossa.

Figure 1:
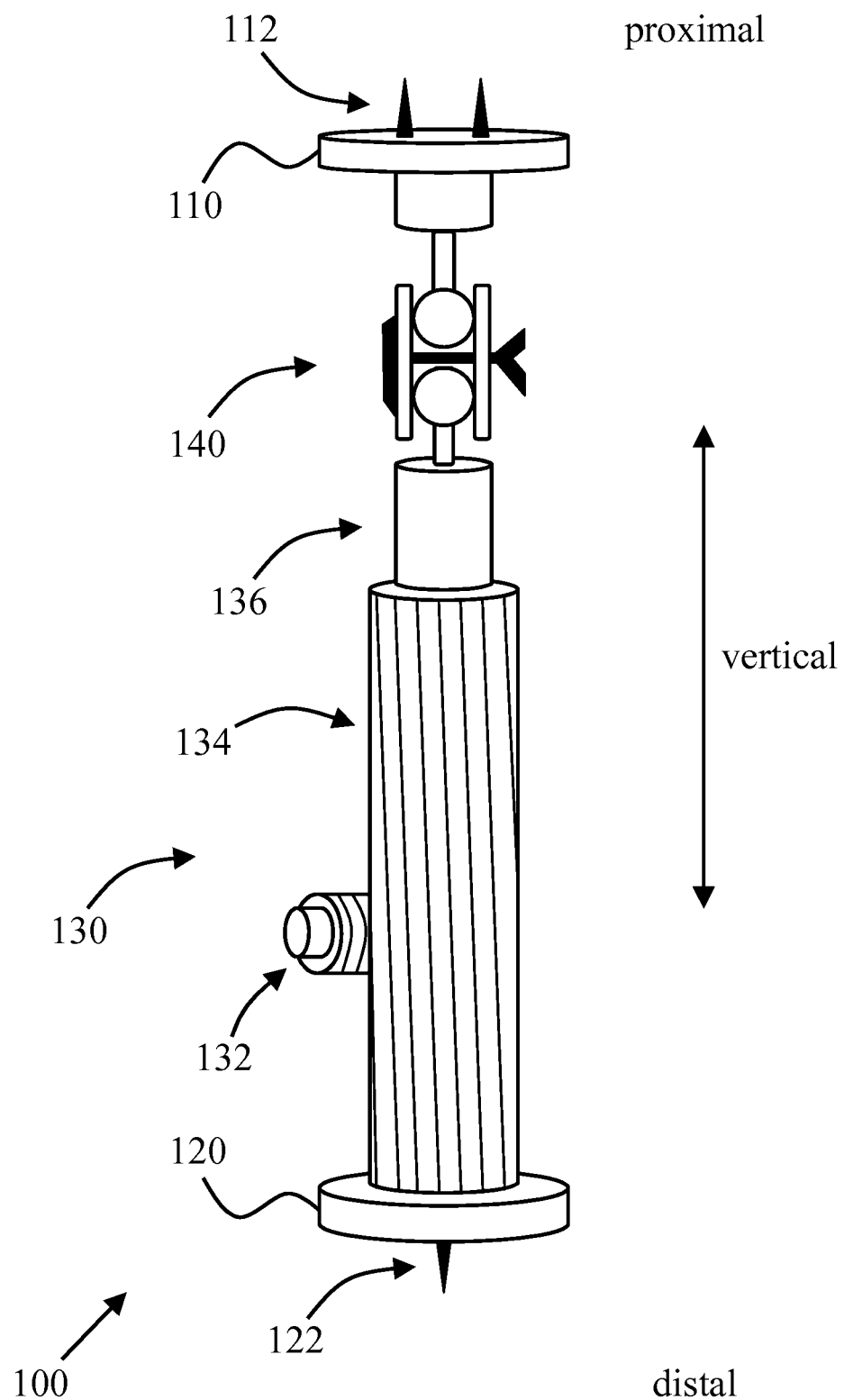
FIG. 1 shows according to an exemplary embodiment of the invention a joint distraction device with a worm gear drive mechanism and a three-dimensional articulating joint connecting the worm gear drive mechanism and the proximal fixation surface.

FIG. 1 shows an exemplary joint distraction device 100 with a proximal fixation surface 110 and a distal fixation surface 120, both preventing migration into bone. A joint distraction mechanism 130 is situated in between both fixation surfaces, 110, 120. The proximal end of joint distraction mechanism 130 is affixed to proximal fixation surface 110, and the distal end of joint distraction mechanism 130 is affixed to distal fixation surface 120.

Proximal fixation surface 110 has an outer facing surface facing away from joint distraction device 100. Outer facing surface of proximal fixation surface 110 has two or more bone spikes for engagement with a proximal bone segment (e.g., AIIS) proximally located to a joint.

Distal fixation surface 120 has an outer facing surface facing away from joint distraction device 100. Outer facing surface of distal fixation surface 120 has one or more bone spikes for engagement with a distal bone segment (e.g., piriformis) distally located from the joint.

Joint distraction mechanism 130 has a force driving mechanism for changing the relative distance between proximal fixation surface 110 and distal fixation surface 120, and therewith the relative distance of proximal bone segment and distal bone segment, thus changing the space within the joint (e.g., hip). It is noted that joint distraction mechanism 130 is also used for changing the length of device 100 for insertion into and retraction from the patient's body.

In one example, joint distraction mechanism 130 has a worm gear drive mechanism. Worm gear 132 is a special type of helical gear whose helix angle is close to perpendicular with the axis of the gear's drive shaft. Resembling a corkscrew, worm gears 132 are usually produced by wrapping a single tooth around the gear's central axis at a given helix angle.

As worm gear 132 is turned, the tooth is advanced in a direction parallel to the gear's central axis. Worm gears could be meshed with either spur gears or helical gears with a complimentary helix angle to create a drive mechanism. Using this arrangement of gears, rotation about a horizontal axis is translated into rotation about a vertical axis, while using minimal space.

In one example, in place of an ordinary helical gear to mesh with the worm gear, gear teeth with a complimentary helix angle could be formed onto about a 72 mm (about 3 inch) long cylinder 134. A tap hole could be drilled through the length of cylinder 134 and threaded to allow distal fixation surface (or stud) 120 and a threaded rod 136 to be screwed into its opposing ends. The exposed end of threaded rod 136 could then be fixed to an articulating joint or head 140 used to attach to the AIIS. This allows cylinder 134 to unscrew from threaded rod 136 when articulating joint 140 is held fixed. When worm gear 132 is turned along a horizontal axis, it meshes with cylinder 134 and causes it to rotate about its vertical axis.

With articulating joint 140 at one end of device 100 held in a fixed position (i.e., simulating attachment to the AIIS), rotation causes cylinder 134 to unscrew from threaded rod 136. As cylinder 134 is unscrewed, the displacement that this creates presses against a distal fixation surface 120 and creates a force in the vertical direction. When this force is applied across the AIIS and the piriformis, distraction will be produced at the hip joint. Since cylinder 134 can be driven by worm gear 132, but not vice-versa, the worm gear drive mechanism in device 100 is self-locking and will hold the generated distraction until worm gear 132 is turned in reverse to release distraction.

It is noted that worm gear 132 could be driven by something outside the patient's body and stays fairly fixed in space other than rotating to generate the force and therefore separation between proximal and distal points.

The mechanism of attachment to the proximal bone segment (e.g., AIIS) has two features. The first feature is proximal fixation plate 110 with two or more bone spikes 112, similar to bones screws or nails, on the outer facing surface that will engage the proximal bone segment. The second feature is the articulating head 140.

When device 100 is inserted through the cannula and proximal fixation plate 110 is pressed against the AIIS, spikes 112 on the plate's surface will insert a short distance into the AIIS and fix it to the bone. As long as two or more spikes are used on the fixation plate surface, a rigid attachment to the surface of the bone is provided which will help stabilize device 100 during joint distraction. Once proximal fixation plate 110 has been fixed to the AIIS, articulating joint 140 can be maneuvered to direct device 100 toward the piriformis fossa and then locked in a fixed position for hip distraction by a friction or set screw mechanism. Articulating joint 140 can also be loosened and adjusted during distraction to change the orientation of the patient's leg and give the surgeon access to different surfaces within the hip during the procedure.

Figure 2:
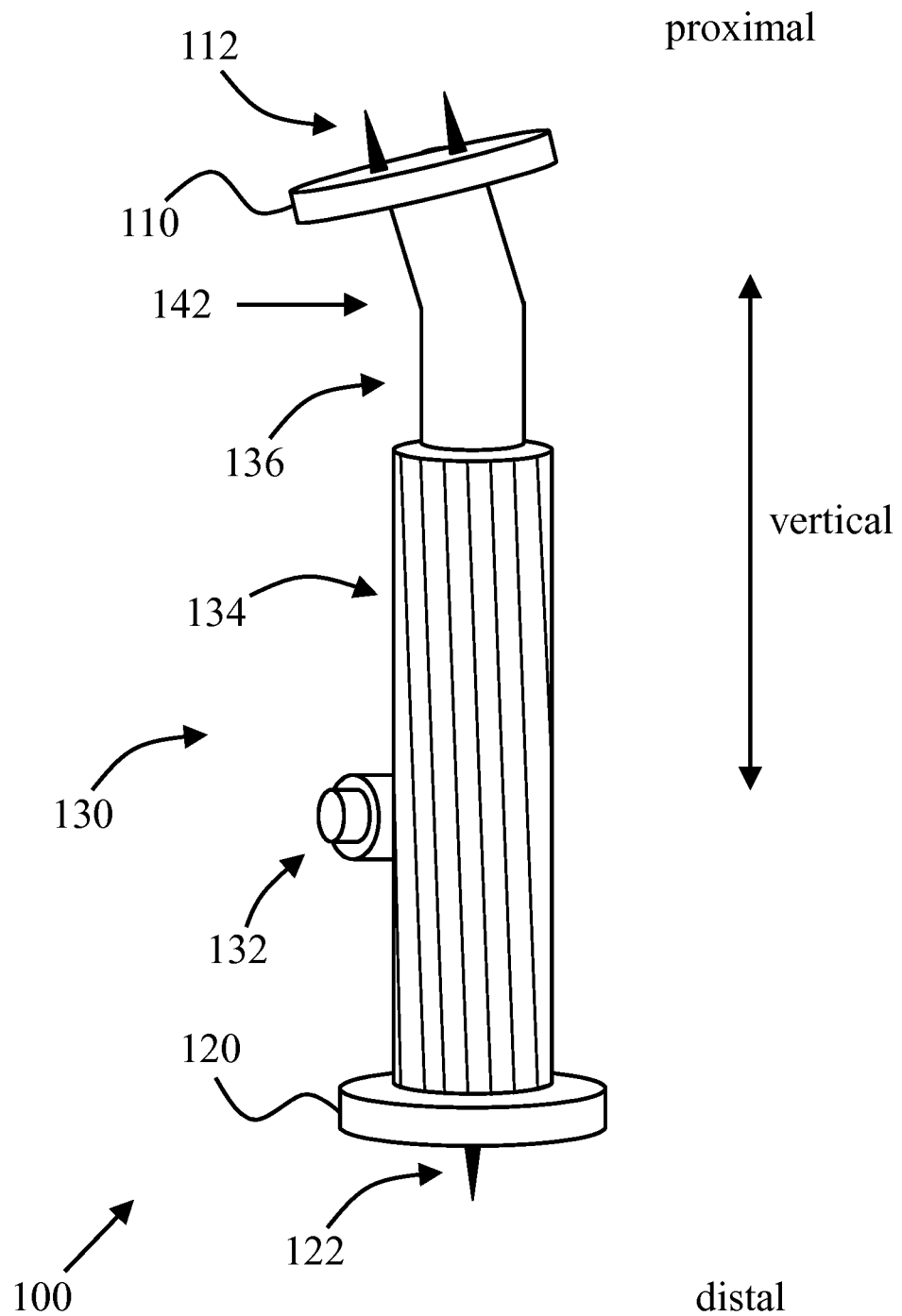
FIG. 2 shows according to an exemplary embodiment of the invention a joint distraction device with a fixed angle in the rod connecting the worm gear drive mechanism and the proximal fixation surface.

It is noted that articulating joint 140 is shown with an exemplary two ball mechanisms that can be clamped together with e.g., a screw or similar fastening mechanism. As a person skilled in the art would appreciate articulating joint 140 could be established with various (joint) mechanisms like a single ball mechanism and is not limited to these examples. In general, the intent of using articulating joint 140 is to align proximal fixation surface 110 against the proximal bone segment (e.g., AIIS) and/or to allow maneuvering of device 100 to point to the opposing bone surfaces. Articulating joint 140 is preferably a three-dimensional articulating joint. However, articulating joint 140 could also have fewer degrees of rotation freedom or even have just a fixed angle (142 in FIG. 2) for aligning the relative position of proximal fixation surface 110 with a proximal bone segment, depending on the type of surgical procedure and/or joint to be distracted.

The mechanism of attachment to the distal bone segment (e.g., piriformis fossa) features a distal fixation plate 120 with one or more bone spikes 122, similar to bones screws or nails, on the outer facing surface that will engage the distal bone segment (i.e., piriformis fossa).

As cylinder 134 unscrews from threaded rod 136 to create distraction, bone spike 122 is pressed into the distal bone segment and holds device 100 in place.

Since the attachment mechanism at the distal end of device 100 is made up of a single point 122, device 100 will be free to rotate with respect to the distal bone segment after bone spike 122 has been pressed into the bone. This will allow device 100 to continue producing a distraction force after both proximal and distal ends have been fixed securely to the bone. Since a larger surface of the distal fixation surface/stud will press against the piriformis fossa once the bone spike has been inserted, the force required to produce distraction will be spread over a larger area and decrease the contact pressure at the proximal femur or piriformis fossa.

Figure 3:
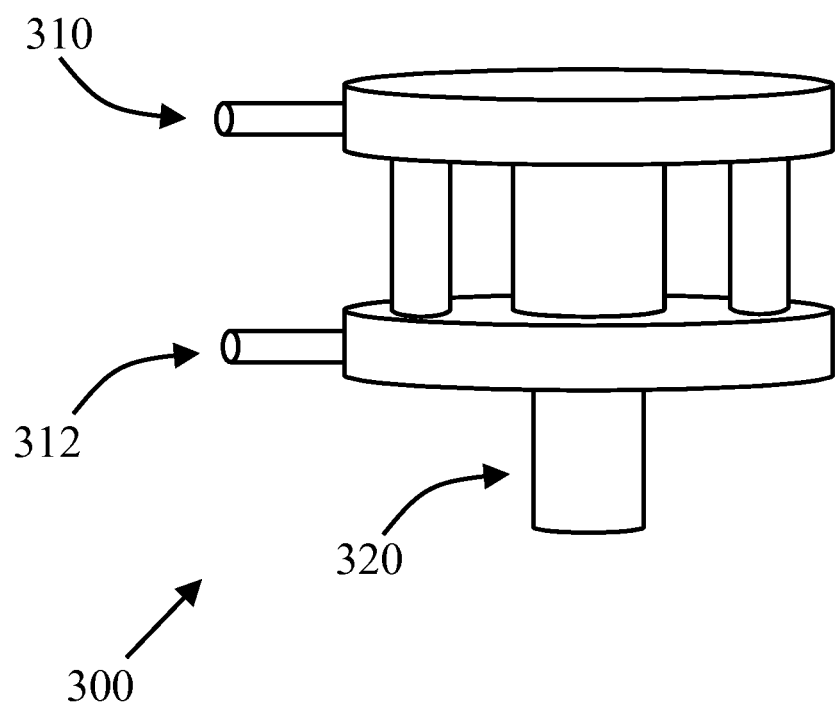
FIG. 3 shows according to an exemplary embodiment of the invention a pneumatic cylindrical force driving mechanism.

In another embodiment, joint distraction mechanism 130 could have a pneumatic cylindrical force driving mechanism shown in FIG. 3. Pneumatic cylinder 300 is powered through a connection to a pressurized air tank or line. The two air inlets 310, 312 are connected to two isolated chambers within the cylinder. When pressurized air is channeled to air inlet 310 via an external switch valve, a piston 320 is extended. When air is channeled to inlet 312, the piston is retracted. This extension of the piston by pressurized air is the mechanism that generates the force applied across the piriformis fossa and the AIIS to generate distraction at the hip.

The mechanism to attach pneumatic cylinder driving mechanism 300 to the AIIS is the same as the one described above in the worm gear device description. Here, the articulating head is instead bonded to the back of the pneumatic cylinder and can be maneuvered to point the piston in the direction of the piriformis fossa. The mechanism to attach pneumatic cylinder 300 mechanism to the piriformis fossa is also similar to the one detailed in the worm gear device description. Here, a bone spike similar to a bone screw or nail is attached to the piston of the pneumatic cylinder. As air pressure pushes the piston toward the piriformis fossa, this spike will embed in the piriformis fossa and fix that end of the device to the bone during distraction.

Exemplary Details:

Devices according to the invention could display various physical measurements depending on the type of surgical procedure, patient size, morphology of the patient's hip (e.g., gender variations), joint or even species. The following is merely an example of measurements for use of the device in hip arthroscopy procedures. It is noted that the invention should not be limited to these exemplary details.

The cannula for insertion and removal of the device could be about 8.25 mm (about 0.32 inches).

The size of the device in shortened position is about 70 mm (about 2.75 inches) and extended position about 102 mm (about 4.0 inches). These sizes could vary about 20% and are based on anatomical differences and device design.

The device attaches to bone using small bone spikes on each end. The force generated through the joint distraction mechanism is sufficient to insert these spikes into bone, which for an exemplary and common cross-section area of screw/pin is about or less than 267 N (60 lbs.).

The one (or more) bone spikes or pins for the piriformis fossa could be about 2-4 mm long and about 1-2 mm in diameter.

The two or more bone spikes or pins on the AIIS side could be about 1 mm long and about 1 mm in diameter.

The proximal and distal joint facing fixation surfaces for the AIIS and proximal femur could each be about 50 $mm^2$.

In one variation, the number of bone spikes at the proximal fixation surface could be one or more provided sufficient fixation (where the articulating mechanism could play a role) to hold the proximal end of the device in place during expansion/distraction.

The force distraction vector generated by the device onto the bone surfaces is preferably as close as possible and as close to be parallel to the joint axis that is being distracted. This would reduce the amount of force required to distract the hip as well as further improve safe distraction.

We claim:

1. A joint distraction device for use in an arthroscopic surgery, comprising:
   (a) a proximal fixation surface;
   (b) a distal fixation surface; and
   (c) a joint distraction mechanism, situated in between the proximal and distal surfaces, having a proximal end affixed to the proximal fixation surface and having a distal end affixed to the distal fixation surface,
   wherein the proximal fixation surface has an outer facing surface facing away from the joint distraction device, and wherein the outer facing surface of the proximal fixation surface has two or more bone spikes for engagement with a proximal bone segment proximally located to a joint,
   wherein the distal fixation surface has an outer facing surface facing away from the joint distraction device, wherein the outer facing surface of the distal fixation surface has one or more bone spikes for engagement with a distal bone segment distally located from the joint,
   wherein the joint distraction mechanism comprises a force driving mechanism for changing the relative distance between the proximal fixation surface and the distal fixation surface, and wherein the force generated by the force driving mechanism should be sufficient to insert the bone spikes into the respective bone segments, as well as distract the joint to create a sufficient enough joint space to allow an intended procedure, and
   wherein the distraction device has a size between the proximal and distal fixation surfaces that is adjustable between a shortened position for introduction before distracting the joint that is between about 56-84 mm, and an extended position for distracting the joint that is between about 81.6-122.4 mm,
   wherein the distal distraction surface has only one bone spike.

2. The joint distraction device as set forth in claim 1, wherein the joint distraction mechanism comprises an articulating joint for aligning the relative position of the proximal fixation surface with the proximal bone segment.

3. The joint distraction device as set forth in claim 2, wherein the articulating joint is a three-dimensional articulating joint.

4. The joint distraction device as set forth in claim 1, wherein the articulating joint can be locked or fixed in a position.

5. The joint distraction device as set forth in claim 1, wherein the joint distraction device can be arthroscopically inserted within a body.

6. The joint distraction device as set forth in claim 1, wherein the spikes are connected substantially perpendicular to the respective outer surfaces of the fixation surfaces.

7. The joint distraction device as set forth in claim 1, wherein the force driving mechanism comprises a worm gear force driving mechanism or a pneumatic force driving mechanism.

8. A method for performing arthroscopic surgery on a patient, comprising:
  providing a distraction device comprising a proximal fixation surface, a distal fixation surface, and a joint distraction mechanism therebetween;
  engaging one or more features on the proximal fixation surface with a proximal bone segment proximally located to a joint of the patient;
  engaging one or more features on the distal fixation surface with a distal bone segment distally located from the joint;
  actuating the joint distraction mechanism to change the relative distance between the proximal fixation surface and the distal fixation surface to drive the one or more features into the respective proximal bone segment and distal bone segment and distract the joint to create a joint space; and
  performing a surgical procedure via the joint space,
  wherein the joint is a hip joint, the proximal bone segment is area on the patient's pelvis, and the distal bone segment is an area on the patient's femur, and
  wherein the area on the patient's pelvis is the anterior inferior iliac spine.

9. The method of claim 8, wherein the joint distraction mechanism comprises an articulating joint, the method further comprising:
  adjusting the articulating joint to direct the distal fixation surface towards the distal bone segment; and
  locking the articulating joint to fix the distraction device in a fixed position.

10. The method of claim 9, further comprising loosening and adjusting the articulating joint during the actuating step to change the relative orientation of the distal bone segment relative to the proximal bone segment.

11. The method of claim 8, wherein the area on the patient's femur is the piriformis fossa.

12. The method of claim 8, further comprising introducing the distraction device arthroscopically into the patient's body.

13. The method of claim 12, wherein the distraction device is introduced into the patient's body via a cannula.

14. The method of claim 8, further comprising removing the distraction device upon completing the surgical procedure.

15. The joint distraction device of claim 1, further comprising a cannula sized for insertion into a joint space and wherein the joint distraction device is sized for insertion into the joint space through the cannula.

* * * * *